United States Patent [19]

Andrea et al.

[11] Patent Number: 4,494,981

[45] Date of Patent: Jan. 22, 1985

[54] USE OF CERTAIN PYRIMIDO[5,4-e]-1,2,4-TRIAZINES FOR CONTROLLING THE GROWTH OF UNWANTED PLANTS

[75] Inventors: Tariq A. Andrea, Escalon; William W. John; James J. Steffens, both of Modesto, all of Calif.

[73] Assignee: Shell Oil Company, Houston, Tex.

[21] Appl. No.: 525,061

[22] Filed: Aug. 22, 1983

[51] Int. Cl.³ .................... A01N 43/64; A01N 43/10
[52] U.S. Cl. ............................................. 71/93; 71/90
[58] Field of Search ...................................... 71/93, 90

[56] References Cited

U.S. PATENT DOCUMENTS 3,609,148  9/1971  Hoegerle et al. ................... 71/93 X
3,759,910  9/1973  Dickore et al. ..................... 71/93 X
3,907,769  9/1975  Jewell et al. ....................... 71/93 X

OTHER PUBLICATIONS

Temple, Jr. et al., J. Org. Chemistry, vol. 28 (1963), pp. 3038–3041.

*Primary Examiner*—Catherine L. Mills

[57] ABSTRACT

The growth of unwanted plants is controlled by certain pyrimido[5,4-e]-1,2,4-triazines.

1 Claim, No Drawings

USE OF CERTAIN PYRIMIDO[5,4-e]-1,2,4-TRIAZINES FOR CONTROLLING THE GROWTH OF UNWANTED PLANTS

DESCRIPTION OF THE INVENTION

It has been found that growth of certain plants is adversely affected by pyrimido[5,4-e]-1,2,4-triazines of the formula:

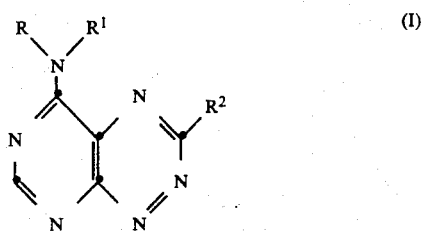

wherein R is hydrogen or alkyl of from one to four carbon atoms, $R^1$ is hydrogen, optionally substituted alkyl of from one to ten carbon atoms, optionally substituted phenyl, or cycloalky of from three to six carbon atoms, and $R^2$ is hydrogen, or is alkyl, or mono- or polyhaloalkyl of from one to six carbon atoms.

In these compounds, each alkyl moiety may be either straight-chain or branched-chain in configuration. Suitable substituents on the alkyl moiety include one or more halogen atoms (bromine, chlorine, fluorine or iodine), hydroxy, alkoxy, alkylthio, alkenyl, alkynyl, cycloalkyl of from three to six carbon atoms, optionally substituted phenyl, or aromatic heterocyclyl selected from furanyl, pyrrolyl, pyridyl, thienyl, thiazolyl, oxazolyl, imidazolyl, pyrimidinyl, and pyrazinyl. In the cases of the halogen and hydroxy moieties, the substituent is bonded to a carbon atom of the alkyl moiety other than the carbon atom thereof that is bonded to the indicated nitrogen atom. Suitable substituents on the phenyl moiety include halogen, mono- and polyhaloalkyl, cyano, nitro, amino, mono- and dialkylamino, alkyl, alkoxy and alkylthio. In all of these substituent moieties, each alkyl suitably contains from one to four carbon atoms, and is either straight-chain or branched-chain in configuration.

5-Amino-3-methylpyrimido[5,4-e]-1,2,4-triazine, and its 3-ethyl counterpart (Formula I, R and $R^1$ each is hydrogen, $R^2$ is methyl and ethyl, respectively) are known compounds, as is 5-(benzylamino)-3-ethyl-pyrimido[5,4-e]-1,2,4-triazine (R is hydrogen, $R^1$ is benzyl, $R^2$ is ethyl): Carroll Temple, Jr. and John A. Montgomery, Journal of Organic Chemistry, volume 28, pages 3038-41 (1963). That article teaches methods which can be used to prepare congeners of these compounds coming within the terms of Formula I.

As shown in the examples hereinafter, Compounds of Formula I can be prepared from 5-(benzylthio)-pyrimido[5,4-e]-1,2,4-triazine, which together with a method for its preparation is disclosed by Carroll Temple, Jr., et al., Journal of Organic Chemistry, volume 34, pages 3161-65 (1969). That article also discloses the method for amination of that compound, which comprises treating it with an excess of the appropriate amine, $R^1R^2NH$, in an alkanol as solvent. Isopropyl alcohol is a convenient solvent. This method is further illustrated and exemplified in the following examples, which describe the preparation, isolation and physical properties of typical individual species of the compounds of Formula I, in particular instances. In each case, the identity of each product, and each of any intermediate involved, was confirmed by appropriate chemical and spectral analyses.

EXAMPLE 1−5-Amino-3-ethylpyrimido[5,4-e]-1,2,4-triazine (1)

Temple and Montgomery, supra, a brown solid, m.p.: 210°-213° C.

EXAMPLE 2−5-(Benzylamino)pyrimidino[5,4-e]-1,2,4-triazine (2)

0.4 g of 5-(benzylthio)pyrimido[5,4-e]-1,2,4-triazine (2A) (Temple, et al., supra), 0.86 ml of benzylamine and 15 ml of isopropyl alcohol were mixed at room temperature and the mixture was stirred for one hour. The mixture then was stripped, ether was mixed and stirred with the residue for 15 minutes, and the resulting mixture was filtered. The solid was dissolved in ethyl acetate, then hexane was added until a cloud point was attained. The crystals were collected to give 2, m.p.: 164°-168° C.

EXAMPLE 3−5-(Ethylamino)pyrimidino[5,4-e]-1,2,4-triazine (3)

1.3 ml of ethylamine was added drop-by-drop rapidly to a stirred suspension of 1.0 g of 2A in 7.5 ml of isopropyl alcohol at room temperature. The resulting mixture was held in a refrigerator over a weekend. Filtration gave 3, as bronze crystals, m.p.: 168°-169° C. The filtrate was concentrated and the residue was crystallized from isopropyl alcohol to give additional 3, as orange crystals, m.p.: 168°-171° C.

EXAMPLES 4-16

By the procedures described in Examples 2 and 3, the following further individual species of the compounds of Formula I were prepared from 2A ($R^2=H$) and the appropriate amines:

| Example No. | Compound No. | R | $R^1$ | Physical Character/Melting Points (°C.) |
|---|---|---|---|---|
| 4 | 4 | H | methyl | Yellow solid/200-262° C. (with decomposition) |
| 5 | 5 | methyl | methyl | orange solid/179-182° C. (with decomposition) |
| 6 | 6 | H | H | brown solid/286-289° C. (with decomposition) |
| 7 | 7 | H | cyclopentyl | orange-yellow solid/110-114° C. |
| 8 | 8 | H | phenyl | orange solid/223-225° C. |
| 9 | 9 | H | 3-methylbutyl | orange-yellow solid/119-126° C. |
| 10 | 10 | H | 4-hydroxypentyl | brown solid/129-140° C. |
| 11 | 11 | H | 2-chlorobenzyl | yellow solid/173-176° C. |
| 12 | 12 | H | 2-(propyloxy)ethyl | yellow solid/194-101° C. |
| 13 | 13 | H | cyclobutyl | orange solid/180-183° C. |
| 14 | 14 | H | 4-pyridylmethyl | orange solid/179-184° C. |

-continued

| Example No. | Compound No. | R | R¹ | Physical Character/Melting Points (°C.) |
|---|---|---|---|---|
| 15 | 15 | H | 2-furanylmethyl | orange solid/149–151° C. |
| 16 | 16 | H | isopropyl | orange solid/150–156° C. |

Compounds of Formula I have been found to adversely affect the growth of some plants, many of which are commonly considered as weeds, and therefore to be useful for controlling the growth of such unwanted plants. Compounds of Formula I have been found to have selectivity with respect to some crop plants—i.e., they control weeds at dosages at which they do not significantly harm the crop plants. While compounds of Formula I appear to have activity when applied preemergence or preplant incorporated (applied to the soil before the seeds have sprouted), most appear to be more effective when applied postemergence (applied to the foliage of the growing plant).

Accordingly, the invention includes a method of combatting unwanted plants which comprises applying to the locus an effective amount of a compound of Formula I. In the cases where it is desired to control weeds in crop plantings, it is of course preferable to employ the lowest dosage that will control the weeds, for this will minimize any possible deleterious effect of the compound upon the crop plants. For application, the compound generally is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula I.

The term "carrier" as used herein means an inert solid or fluid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable fluid carriers are water, alcohols such as, for example, isopropyl alcohol, glycols; ketones such as, for example, acetone, methyl ethyl ketone, methyl isobutyl ketone and cyclohexanone; ethers such as, for example, cellosolves; aromatic hydrocarbons such as, for example, benzene, toluene and xylene; petroleum fractions such as, for example, kerosene, light mineral oils; chlorinated hydrocarbons such as, for example, carbon tetrachloride, perchloroethylene, trichloroethane, including liquefied, normally vaporous, gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkyl-aryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25, 50 or 75% by weight of the active compound and usually contain, in addition to the solid carrier, 3–10% by weight of a dispersing agent, 15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick, mayonnaise-like consistency.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound of Formula I will be satisfactory.

EXAMPLES OF ACTIVITY WITH RESPECT TO PLANTS

In the following examples, the species of plants that were tested were:

Barnyardgrass (watergrass)-*Echinochloa crus-galli*
Large crabgrass-*Digitaria sanguinalis*
Downy brome-*Bromus tectorum*
Yellow foxtail-*Setaria lutescens*
Redroot pigweed-*Amaranthus retroflexus*
Sicklepod-*Cassia obtusifolia*
Velvetleaf *Abutilon theophrasti*
Garden cress-*Lepidium sativum*
Johnsongrass-*Sorghum halepense*

TEST PROCEDURES

The preemergence (soil) herbicidal activity of the compounds was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 20 and 2.0 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3-4 | Observable damage |
| 1-2 | Plant slightly affected, possibly by the chemical, possibly due to biological variability |
| 0 | No visible effect |

The postemergence (foliar) herbicidal activity of compounds of the invention was evaluated by spraying 10-day-old large downy brome plants in some cases, 6-day-old Johnsongrass plants in other cases, 9-day-old velvetleaf plants, 9-day-old yellow foxtail plants and 9-day-old sicklepod plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days, and the effect of the test compound was then evaluated visually, the results being rated on the 0 to 9 scale described above.

Results of the preemergence and postemergence herbicidal activity tests are set forth in Table I.

TABLE I

| | HERBICIDAL ACTIVITY | | | | | | | | | | | |
| --- | --- | --- | --- | --- | --- | --- | --- | --- | --- | --- | --- | --- |
| | Preemergence | | | | | | Postemergence | | | | | |
| Compound | Barnyard-grass | Garden Cress | Downy Brome | Velvet-leaf | Yellow Foxtail | Sickle-pod | Crab-grass | Pig-weed | Johnson-grass | Velvet-leaf | Yellow Foxtail | Sickle-pod |
| 1 | 7 | 8 | 0 | 3 | 0 | 0 | 7 | 9 | 5 | 7 | 7 | 4 |
| 2 | 9 | 9 | 8 | 5 | 8 | 6 | 6 | 9 | 4 | 6 | 2 | 2 |
| 3 | 9 | 9 | 3 | 5 | 3 | 2 | 9 | 9 | 4 | 8 | 5 | 4 |
| 4 | 8 | 9 | 2 | 2 | 0 | 0 | 9 | 9 | 7 | 7 | 5 | 5 |
| 5 | 2 | 8 | 0 | 3 | 0 | 2 | 8 | 9 | 4 | 7 | 2 | 3 |
| 6 | 9 | 9 | 4 | 2 | 0 | 2 | 7 | 9 | 6 | 6 | 6 | 2 |
| 7 | 8 | 9 | 5 | 4 | 5 | 6 | 9 | 9 | 3 | 5 | 5 | 4 |
| 8 | 9 | 9 | 7 | 7 | 7 | 6 | 8 | 9 | 6 | 2 | 6 | 3 |
| 9 | 9 | 9 | 7 | 7 | 6 | 6 | 8 | 9 | 5 | 4 | 4 | 5 |
| 10 | 7 | 8 | 0 | 2 | 0 | 3 | 9 | 9 | 4 | 3 | 3 | 2 |
| 11 | 7 | 8 | 6 | 0 | 7 | 0 | 4 | 8 | 5 | 4 | 8 | 3 |
| 12 | 8 | 9 | 3 | 2 | 7 | 2 | 4 | 9 | 4 | 5 | 2 | 3 |
| 13 | 9 | 9 | 3 | 0 | 3 | 0 | 9 | 9 | 5 | 5 | 4 | 3 |
| 14 | 8 | 8 | 3 | 0 | 0 | 0 | 9 | 9 | 5 | 3 | 6 | 3 |
| 15 | 7 | 8 | 7 | 2 | 6 | 2 | 7 | 9 | 3 | 6 | 6 | 3 |

TABLE I-continued

HERBICIDAL ACTIVITY

| Compound | Preemergence | | | | | | Postemergence | | | | | |
|---|---|---|---|---|---|---|---|---|---|---|---|---|
| | Barnyard-grass | Garden Cress | Downy Brome | Velvet-leaf | Yellow Foxtail | Sickle-pod | Crab-grass | Pig-weed | Johnson-grass | Velvet-leaf | Yellow Foxtail | Sickle-pod |
| 16 | 9 | 9 | 7 | 8 | 6 | 7 | 9 | 9 | 7 | 6 | 6 | 6 |

EXAMPLES OF SELECTIVITY

In the following examples, the species of plants that were tested were:
  Barnyardgrass
  Downy brome
  Johnsongrass
  Wild oats-*Avena fatua*
  Yellow foxtail
  Goose grass-*Eleusine indica* L.
  Yellow nutsedge-*Cyperus esculentus* L.
  Cocklebur-*Xanthum pennsylvanicum*
  Morning glory-*Ipomoea purpurea* L. (Roth)
  Wild mustard-*Brassica kaber*
  Redroot pigweed
  Sicklepod
  Velvetleaf
  Corn-*Zea mays*
  Cotton-*Gossypium hirsutum*
  Rice-*Oryza sativa*
  Grain sorghum-*Sorghum vulgare*
  Soybeans-*Glycine max*
  Sugarbeets-*Beta vulgaris*
  Wheat-*Triticum aestivum*
  Nightshade-*Solanum nigrum* sp.

TEST PROCEDURES

The preemergence activity of compounds of Formula I was further determined with respect to certain species of crop plants and common species of weeds, by spraying a formulation of the test compound on soil in small pots in which seeds of the plants had been sown. The postemergence herbicidal activity of compounds of Formula I was evaluated with respect to the crop plants and weeds, by spraying a formulation of the test compound on the foliage of the young growing plants. In each series of tests, the plants were grown in narrow trays and sprayed with the formulation. Dosages of the test compounds of 2.0 pounds/acre in some cases, and 1.0 or 0.25 pound/acre in all cases, were used. The results of the tests were evaluated on the basis of the 0-9 scale described with respect to the earlier tests. Activity of the test compound in such case was characterized as follows:

| | Dosage (lb/acre) | Rating (one or another) |
|---|---|---|
| Highly active | 0.25 | 8-9 |
| | 1.0 | 8-9 |
| | 2.0 | 8-9 |
| Very active | 0.25 | 6-7 |
| | 1.0 | 8-9 |
| | 2.0 | 8-9 |
| Active | 0.25 | 4-5 |
| | 1.0 | 6-7 |
| | 2.0 | 7-9 |
| Slightly active | 0.25 | 2-3 |
| | 1.0 | 3-4 |
| | 2.0 | 4-5 |
| Essentially inactive | 0.25 | 0 |
| | 1.0 | 0-3 |
| | 2.0 | 1-3 |

Compounds 1, 2, 9 and 16 were tested preemergence: Compound 1 was essentially inactive with respect to all of the varieties of test plants at dosages of 1.0 and 0.25 pounds/acre. At dosages of 1.0 and 0.25 pounds/acre, Compound 2 was highly active with respect to mustard, very active with respect to goose grass and slightly active to active with respect to corn, grain sorghum, barnyardgrass and Johnsongrass. At 0.25 pound/acre, Compound 9 was essentially inactive with respect to all of the plants except sugarbeets, with respect to which it was highly active. At 0.25 pound/acre, Compound 16 was essentially inactive with respect to all of the plants except morningglory, with respect to which it was highly active, and soybeans, with respect to which it was active.

|  |  |
|---|---|
| Corn: | highly active: Compound 3; very active: Compound 9; active: Compound 8; slightly active: Compounds 1, 7 and 11; essentially inactive: Compound 4. |
| Cotton: | Highly active: Compounds 3, 4, 7-9; essentially inactive to slightly active: remainder. |
| Johnsongrass: | active: Compound 3; the rest were essentially inactive to slightly active. |
| Wild oats: | active: Compound 3; the rest were essentially inactive to slightly active. |
| Goose grass: | inactive to slightly active. |
| Yellow foxtail: | Very active: Compound 3; all the rest were essentially inactive to slightly active. |
| Yellow nutsedge: | All of the compounds were essentially inactive. |
| Cocklebur: | highly active: Compound 7; active: Compounds 3, 4, 9; essentially inactive: Compound 8. Compounds 1 and 11 were not tested with respect to his variety of plant. |
| Morningglory: | highly active: Compounds 3 and 9; active Compounds 1 and 11. |
| Rice: | slightly active: Compound 3; all the rest were essentially inactive. |
| Grain sorghum: | active: Compounds 3 and 9; slightly active: Compounds 4 and 7; essentially inactive: Compounds 1, 8 and 11. |
| Soybeans: | very active: Compound 3; all the rest were active. |
| Sugar beets: | highly active: Compound 3; very active Compound 7; active: Compounds 1, 4, 8 and 11; slightly active: Compound 9. |
| Wheat: | active: Compound 3; slightly active: Compounds 4, 7 and 9; essentially inactive: Compounds 1, 8 and 11. |
| Barnyard grass: | slightly active: Compounds 3, 4, 7 and 9; essentially inactive: Compounds 1, 8 and 11. |
| Downy Brome: | slightly active: Compounds 1, 3, 4, 7 and 9; essentially inactive: Compounds 8 and 11. |
| Mustard: | highly active: Compounds 3 and 7; very active: Compounds 1, 4 and 9; active: Compound 11; essentially inactive: Compound 8. |
| Pigweed: | highly active: Compounds 1, 3, 4 and 7; very active: Compound 9; active: Compounds 8 and 11. |
| Sicklepod: | highly active: Compounds 3 and 7; |

-continued

| | |
|---|---|
| | active: Compounds 1, 4 and 9; slightly active: Compounds 1 and 11; essentially inactive: Compound 8. |
| Velvetleaf: | highly active: Compound 3; very active: Compounds 4 and 7; active: Compound 9; slightly active: Compounds 1 and 8; essentially inactive: Compound 11. |
| Nightshade: | highly active: Compounds 3, 4, 7 and 9; very active: Compound 1; active: Compound 8; essentially inactive: Compound 11. |

We claim:

1. A method for controlling the growth of unwanted plants at a locus, which method comprises applying to the locus an effective amount of a compound of the formula

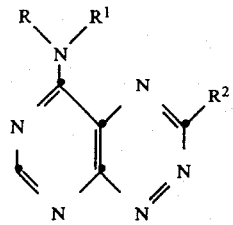

(I)

wherein R is hydrogen or alkyl of from one to four carbon atoms, $R^1$ is hydrogen or optionally substituted alkyl of from one to ten carbon atoms, either straight-chain or branched-chain in configuration, any substituent thereon being selected from: (a) halogen and hydroxy, bonded to a carbon atom other than the carbon atom of the alkyl moiety that is bonded to the indicated nitrogen atom; (b) alkoxy, alkylthio, alkenyl, alkynyl, cycloalkyl of from three to six carbon atoms; (c) optionally substituted phenyl, any substituent thereon being selected from halogen, mono- and polyhaloalkyl, cyano, nitro, amino, mono- and dialkylamino, alkyl, alkoxy and alkylthio wherein each alkyl moiety contains from one to four carbon atoms; and (c) aromatic heterocyclyl selected from furanyl and pyridyl, and $R^2$ is hydrogen or is alkyl, or mono- or polyhaloalkyl of from one to six carbon atoms.

* * * * *